United States Patent [19]

Kemp

[11] 4,374,526

[45] Feb. 22, 1983

[54] HEARING FACULTY TESTING AND APPARATUS THEREFOR

[75] Inventor: David T. Kemp, Hatfield, England

[73] Assignee: National Research Development Corporation, London, England

[21] Appl. No.: 230,957

[22] PCT Filed: Feb. 9, 1979

[86] PCT No.: PCT/GB79/00030

§ 371 Date: Oct. 10, 1979

§ 102(e) Date: Aug. 14, 1979

[87] PCT Pub. No.: WO79/00614

PCT Pub. Date: Sep. 6, 1979

[30] Foreign Application Priority Data

Feb. 10, 1978 [GB] United Kingdom ............... 5467/78

[51] Int. Cl.³ ............................................. A61B 5/12
[52] U.S. Cl. ...................................... 128/746; 73/585; 179/1 N
[58] Field of Search ............... 128/746; 73/585, 589; 179/1 N

[56] References Cited

U.S. PATENT DOCUMENTS

| | | | |
|---|---|---|---|
| 3,294,193 | 12/1966 | Zwislocki | 73/585 |
| 3,395,697 | 10/1968 | Mendleson | 128/746 |
| 3,757,769 | 9/1973 | Arguimbau et al. | 128/746 |
| 3,882,848 | 5/1975 | Klar et al. | 128/746 |
| 3,949,735 | 4/1976 | Klar | 128/746 |
| 4,002,161 | 1/1977 | Klar et al. | 128/746 |
| 4,009,707 | 3/1977 | Ward | 128/746 |
| 4,057,051 | 11/1977 | Kerouac | 128/746 |
| 4,079,198 | 3/1978 | Bennett | 128/746 |

Primary Examiner—Kyle L. Howell
Assistant Examiner—John C. Hanley
Attorney, Agent, or Firm—Cushman, Darby & Cushman

[57] ABSTRACT

A hearing faculty test and apparatus therefor is based on the findng that sound input to the ear gives rise to a returned wave from and related to the condition of the inner ear, this wave being detectable as an echo from the ear drum. The apparatus preferably comprises a sealing aural probe (1) housing transducers (2,3) respectively to project a repetitive transient sound by pulse generator (4) activation and to pick-up for detection (5) successive echoes by time-gating. Detected echoes are preferably averaged during processing (6) for display. The echo occurs about 5–20 ms after its sound and a maximum operating frequency of about 50 Hz is appropriate. A continuous sound input can be used with consequent echo interference detectable as rapid changes of acoustic impedance with sound input frequency. Another alternative can involve detection of the ear drum movement by returned waves.

12 Claims, 1 Drawing Figure

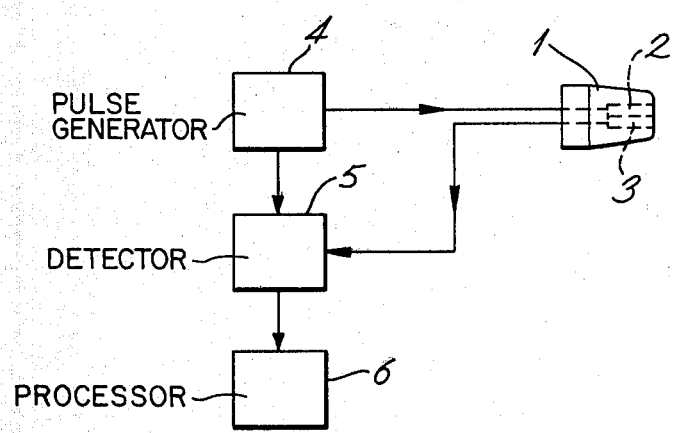

HEARING FACULTY TESTING AND APPARATUS THEREFOR

This invention concerns hearing faculty testing and apparatus therefor.

Quantitative information on the state of the ear can at present be obtained for medical purposes using audiometric tests or through electrophysiological examination. However, these techniques do not fully meet the requirements of the clinician for the early detection, assessment and monitoring of hearing disorders. Difficulties arise with the presently available techniques mentioned above because the first kind demand a high degree of concentration and co-operation from the subject under test, and the second kind ideally involves invasive surgery and, on occasion, sedation. These difficulties are most evident when the subject is a young child.

The present invention improves this situation by making available a further technique which does not suffer from the above difficulties. The invention has arisen from the finding, contrary to present understanding, that the healthy human ear emits a detectable echo in response to receipt of a transient sound and that the echo is related to the characteristics of the sound and the conditions inside the ear. It is to be understood that this echo involves a further movement of the ear drum after the initial movement thereof caused directly by the incident sound pressure variation has decayed to zero relative to currently available detection techniques. Moreover, the echo is sufficiently delayed relative to its causative sound and the associated direct response to allow separation by electronic time-gating, and the echo is considered to be related more specifically to the characteristics of the inner ear and to deteriorate therewith.

Accordingly, in a more general form thereof, the present invention provides hearing faculty testing apparatus comprising means for applying a sound to a subject's ear, and means for detecting the wave returned from the inner ear in response to said sound. The applied sound will normally be of a transient form, but this is not essential since any sound will produce a returned wave. Also, detection of the returned wave will normally be by way of the echo produced thereby, but this is not essential insofar as it is possible to detect the associated movement of the ear drum.

In a more particular form the invention provides hearing faculty testing apparatus comprising an aural probe for insertion in a subject's external ear canal, electroacoustic transducer means mounted in said probe for projecting sound into said canal and responding to an echo produced by said sound in said canal, means for repeatedly activating said transducer means to generate a sequence of transient sounds, time-gating means responsive to both said activating means and said transducer means for detecting signals representing the echoes produced by said sound, analyser means responsive to said detecting means for processing said detected signals at least by averaging a sequence thereof, and display and/or recording means responsive to said processing means.

In order that the invention may be better understood, the same will now be described by way of example with reference to the accompanying drawing which schematically illustrates one form of the invention as developed so far.

The illustrated form of the invention is of the more particular form mentioned above and comprises an aural probe 1 to interface with a patient by location in his external ear canal. This probe is formed to penetrate and effect an air tight seal with the canal and, for this purpose in routine clinical use, a range of shapes and sizes will be necessary to allow for the natural variation between the ears of different patients. Conveniently, use may be made of a range of disposable tips engageable with a common probe base for this last purpose.

Since the probe is to seal with the canal, it may be appropriate to provide a closable air passageway through the probe whereby the pressures about the ear drum can be equalised after location of the probe and before operation of the apparatus.

The probe carries two electroacoustic transducers 2 and 3 for respectively applying transient sound into the canal and responding to the corresponding echo. These transducers suitably comprise a miniature sound source and a ceramic miniature microphone unit, such as used in postaural hearing aids, which are integrated with the probe and communicate directly with the air space between the probe and ear drum. The forms of such transducers used in initial development provide frequency ranges of 500–4000 Hz without resonance, with the source being capable of producing sound pressure levels of 90 dB per 2 cc. volume, and with the sensitivity and noise level of the microphone being such that the equivalent noise input level is less than 30 dB A. The frequency responses of the transducers are preferably as flat as possible.

The sound source is operably connected to a pulse generator 4 which, in the development so far, provides pulses of less than 200 μs width and adjustable amplitude, such as to give aural spectral densities of between −30 and +40 dB SPL/Hz. The generator used in initial development has been adjustable in respect of pulse frequency, and a maximum useful frequency of about 50 Hz, has been found to arise in practice because the echoes overlap with the succeeding pulses at higher frequency. In practice it will be appropriate usually to employ a frequency just below this maximum to reduce the necessary overall time of operation as far as possible. Also, the generator has been provided with a facility allowing operation in an irregular manner to facilitate use only during quiet periods of environmental and subject-generated noise, but in further development it is thought that it may be appropriate to inhibit application of echoes to the processor (discussed below) by automatic operation in response to such noise.

The microphone and pulse generator are connected to a detector 5 which preamplifies the microphone output and then time-gates the echo signal component of this output in delayed synchronism with the pulse generator output. As indicated above, the microphone output is found to comprise a direct signal component and an echo signal component, and these two components are separated in time. The direct component represents the response to the ear drum and the middle ear to the transient sound input, and this component usually effectively terminates within a period of about 5 ms after the initiating sound. The echo component occurs within a further period of about 15 ms thereafter. The echo component is accordingly readily separated and this can be effected by gating the same during a predetermined constant period such as just mentioned or during an appropriate period which is terminated by initiation of the next transient sound input. The echo component is suitably further amplified and applied to a processor 6.

The processor comprises an averager which is suitably responsive to a sequence of 20-2000 echoes. In a simple apparatus the resultant averaged signal can be monitored aurally and/or visually displayed for assessment. Also the averaged signal can be recorded for subsequent, separate analysis. In a more sophisticated apparatus the averaged echo can be subjected to more detailed direct analysis such as by Fourier analysis.

On the basis of the development of the invention so far it can be expected that stimulus levels in a healthy ear of between −20 and +15 dB SPL/Hz will result in echo sound fields in the ear canal of between 10 and 25 dB SPL at maximum, and the dominant frequency component is likely to be between 1 and 2 KHz. Detectable echoes below 10 dB SPL appear indicative of hearing loss, an average mid-frequency loss of 10-20 dB being sufficient to lower the echo to around 0 dB SPL after averaging. The detailed form of the averaged echo appears to vary virtually uniquely between individual patients so that a primary assessment of a patient's condition will be based on echo amplitude rather than comparison with a "standard" waveform. However, the condition of any one patient can be monitored by comparison of echoes obtained at successive intervals of time.

Echo level does not, of course, prove inner ear disorder because the signal inputs and outputs are transmitted through the middle ear and are therefore subject to the condition of the latter. However, this can be taken into account by differential diagnosis by use of other techniques to test the middle ear. For this last purpose the probe of the present invention may be used to obtain tympanic acoustic impedance measurements. If a normal middle ear is present, analysis of the echoes can provide an indication of cochlear activity, and it appears that the input-output transfer coefficient at individual frequencies are related to the cochlear activity associated with the response of those frequencies.

It is to be noted that the echo is of significantly lesser intensity, about 40 dB, than the associated direct signal and the present preference for use of an ear probe which penetrates and seals the external canal is to minimise the probe/drum space and thereby enhance the pressure variations resulting from the drum movements due to the echo. In practice the probe has been such as to penetrate the canal for not less than 0.75 cm.

It will be appreciated that the invention is capable of modification and further development within the more general discussion thereof given in the introduction of this specification. For example, while the invention has been described more particularly as involving a transient sound input and time-gated echo detection, a continuous sound input can be employed. In this last event, the input is suitably swept over a range of frequencies: the echo then causes interference and is detectable as rapid changes of acoustic impedance with frequency. In one technique of this kind a simple result can be obtained by adjustment of the input to a narrow frequency band giving the best echo output. These techniques preferably employ a low level sound input and narrow band filtering for the output.

Turning lastly to the question of practical application of the invention: it is clear from the above discussion that the invention finds it primary application in clinical and hospital usage to analyse and monitor the hearing faculty of patients. In addition, application can arise in connection with the testing of drugs, the invention being useful in assessing hearing faculty damage which may result as a direct or side effect, such as when determining maximum safe dosages during drum development, and particularly when employing animal tests.

I claim:

1. Hearing faculty apparatus comprising:
an aural probe for insertion in the external canal of a subject's ear,
an electroacoustic transducer detector mounted in said probe to generate signals in response to sound pressure waves returned through said canal by reflection within the associated inner ear and reaction elsewhere, and
signal separation means connected with said transducer to extract, for retention from said signals, components thereof representing substantially exclusively only said inner ear reflection.

2. Apparatus according to claim 1 characterised in that said probe is formed to sealingly penetrate said canal.

3. Apparatus according to claim 2 characterised in that said probe includes a base part housing said transducer, and a replaceable part to engage said canal.

4. Apparatus according to claim 1, 2 or 3 wherein said sound source includes a pulse generator and a further electroacoustic transducer mounted in said probe and responsive to said generator to produce a repetitive transient sound.

5. Apparatus according to claim 4 wherein said signal separation means includes a time gate controlled by said generator to extract for retention from said signals only components occurring during a period from 5-20 ms following termination of each said sound.

6. Apparatus according to claim 4 characterized in that said generator is operable at a frequency not greater than about 50 Hz.

7. Apparatus according to claim 4 characterised by an averager responsive to the output of said separation means to average said retained components.

8. Hearing faculty testing apparatus comprising:
an aural probe for insertion in a subject's external ear canal,
electroacoustic transducer means mounted in said probe for projecting sound into said canal and for responding to reactions produced by said sound in said canal,
a pulse generator for repeatedly activating said transducer means to project a sequence of transient sounds,
time-gating means responsive to both said generator and said transducer means for detecting delayed reactions produced by said sounds only within a period of from 5 to 20 ms following termination thereof to detect the reactions produced exclusively by return of said sound from within the inner ear of said subject, and
analyser means responsive to said detecting means for processing the detected echo signals at least by averaging a sequence thereof.

9. Hearing faculty testing apparatus comprising:
an aural probe for insertion in a subject's external ear canal,
electroacoustic transducer means mounted in said probe for projecting sound into said canal and for responding to reactions produced by said sound in said canal,
a pulse generator for repeatedly activating said transducer means to project a sequence of transient sounds, time-gating means responsive to both said generator and said transducer means for detecting delayed reactions produced by said sounds following termination thereof, said time-gating means being constructed to detect the reactions produced by return of said sounds from within the subject's inner ear substantially only during a period from 5-20 ms, and analyser means responsive to said detecting means for processing the detected reaction signals at least by averaging a sequence thereof.

10. A method of testing hearing faculty comprising: applying a sound to a subject's ear, detecting in electrical signal form the waves returned from the ear in response to said sound by reflection from the inner ear and other reactions, and extracting for retention from said detected electrical signals components thereof representing substantially exclusively only said inner ear reflection.

11. A method according to claim 10 wherein said sound is of repetitive pulse form, and said extraction involves time-gating during a period following termination of each said pulse.

12. A method according to claim 10 wherein said sound is of continuous swept-frequency form and said extraction involves detection of interference between said components for retention and other signal components.

* * * * *